(12) United States Patent
Daniel et al.

(10) Patent No.: US 9,345,575 B2
(45) Date of Patent: May 24, 2016

(54) RESORBABLE SUTURE-ENGAGEMENT COMPONENT FOR A PENILE PROSTHETIC

(71) Applicant: Coloplast A/S, Humlebaek (DK)

(72) Inventors: Geoffrey A. Daniel, Crystal, MN (US); Yelena Tropsha, Plymouth, MN (US)

(73) Assignee: Coloplast A/S, Humlebaek (DK)

( * ) Notice: Subject to any disclaimer, the term of this patent is extended or adjusted under 35 U.S.C. 154(b) by 79 days.

(21) Appl. No.: 14/476,764

(22) Filed: Sep. 4, 2014

(65) Prior Publication Data

US 2016/0067044 A1    Mar. 10, 2016

(51) Int. Cl.
| | |
|---|---|
| *A61F 2/26* | (2006.01) |
| *A61B 17/04* | (2006.01) |
| *A61F 5/41* | (2006.01) |

(52) U.S. Cl.
CPC . *A61F 2/26* (2013.01); *A61B 17/04* (2013.01); *A61F 5/41* (2013.01)

(58) Field of Classification Search
CPC ............. A61F 2/26; A61F 5/41; A61F 5/411; A61F 5/415
USPC ...................................................... 600/38–41
See application file for complete search history.

(56) References Cited

U.S. PATENT DOCUMENTS

| | | | |
|---|---|---|---|
| 4,244,370 | A | 1/1981 | Furlow et al. |
| 5,681,289 | A | 10/1997 | Wilcox et al. |
| 5,868,729 | A | 2/1999 | Pelfrey |
| 2010/0010530 | A1 | 1/2010 | Rhee |
| 2010/0160722 | A1 | 6/2010 | Kuyava et al. |

FOREIGN PATENT DOCUMENTS

| | | |
|---|---|---|
| EP | 0682923 A1 | 11/1995 |
| WO | 2005032428 A1 | 4/2005 |
| WO | 2010043228 A1 | 4/2010 |
| WO | 2011023197 A1 | 3/2011 |

*Primary Examiner* — John Lacyk
(74) *Attorney, Agent, or Firm* — Coloplast Corp., Coloplast A/S; Nick Baumann

(57) ABSTRACT

Disclosed is a penile prosthetic including a cylinder and a resorbable suture-engaging component attached to an exterior surface of the cylinder. The suture-engaging component is attachable to a suture to allow a surgeon to pull the cylinder in a distal direction into the penis. During the healing time after the surgery, the resorbable suture-engaging component is resorbed into the tissue of the penis.

25 Claims, 16 Drawing Sheets

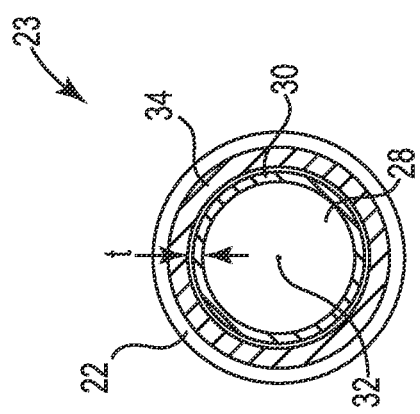

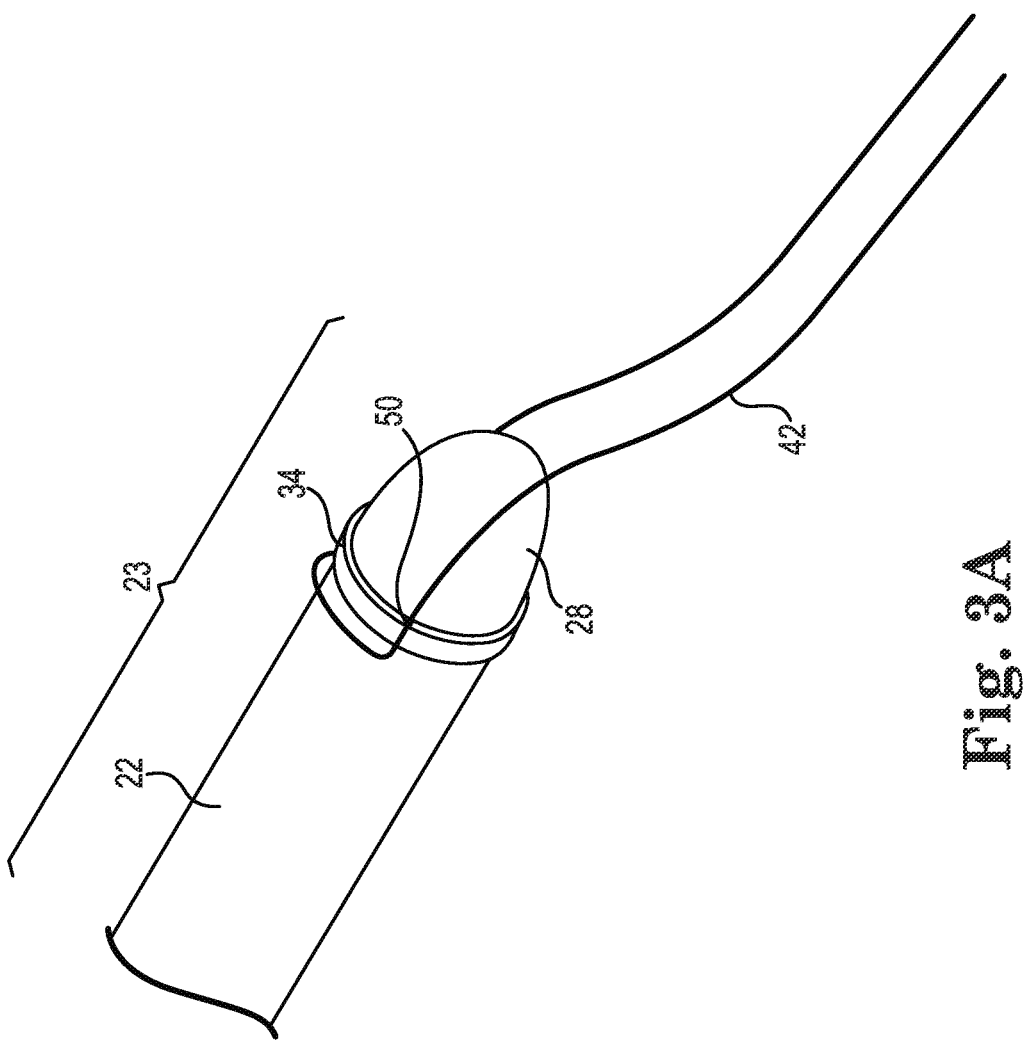

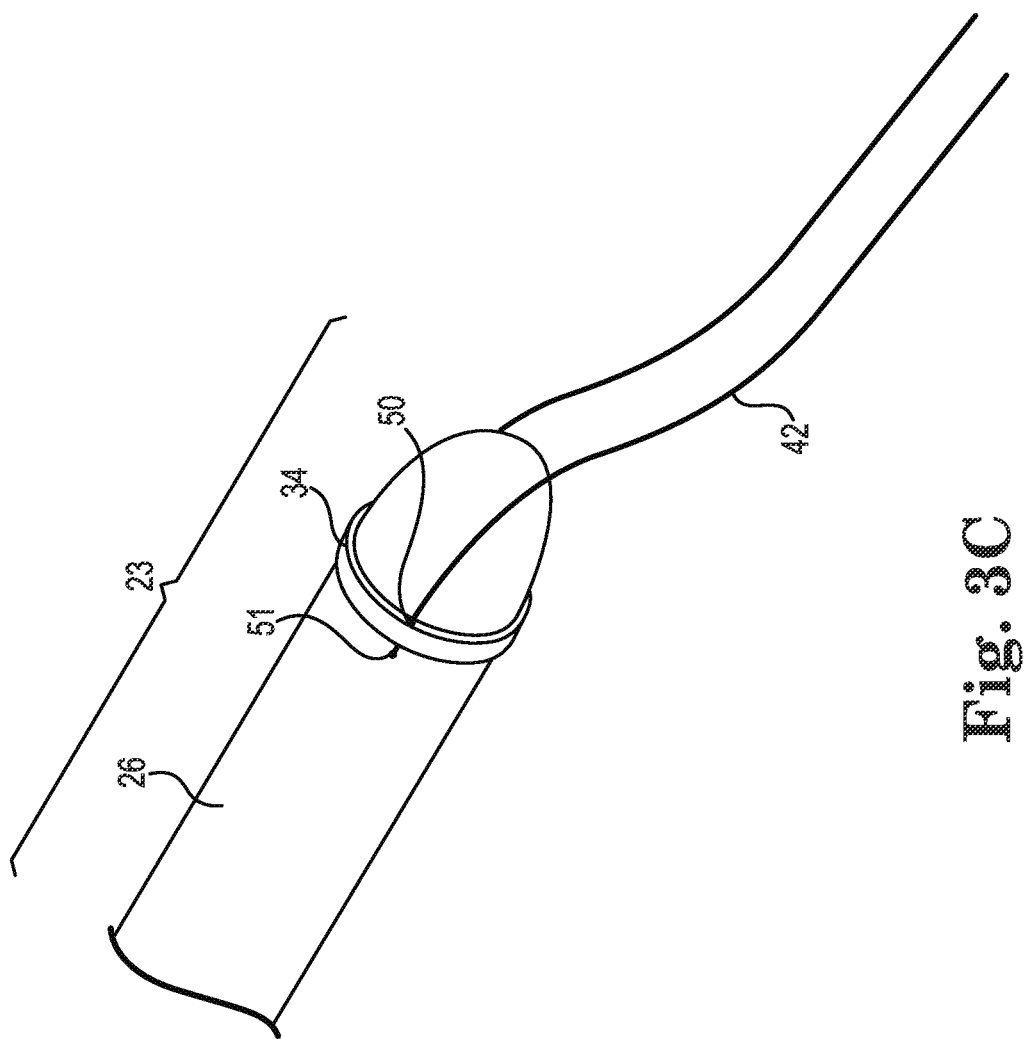

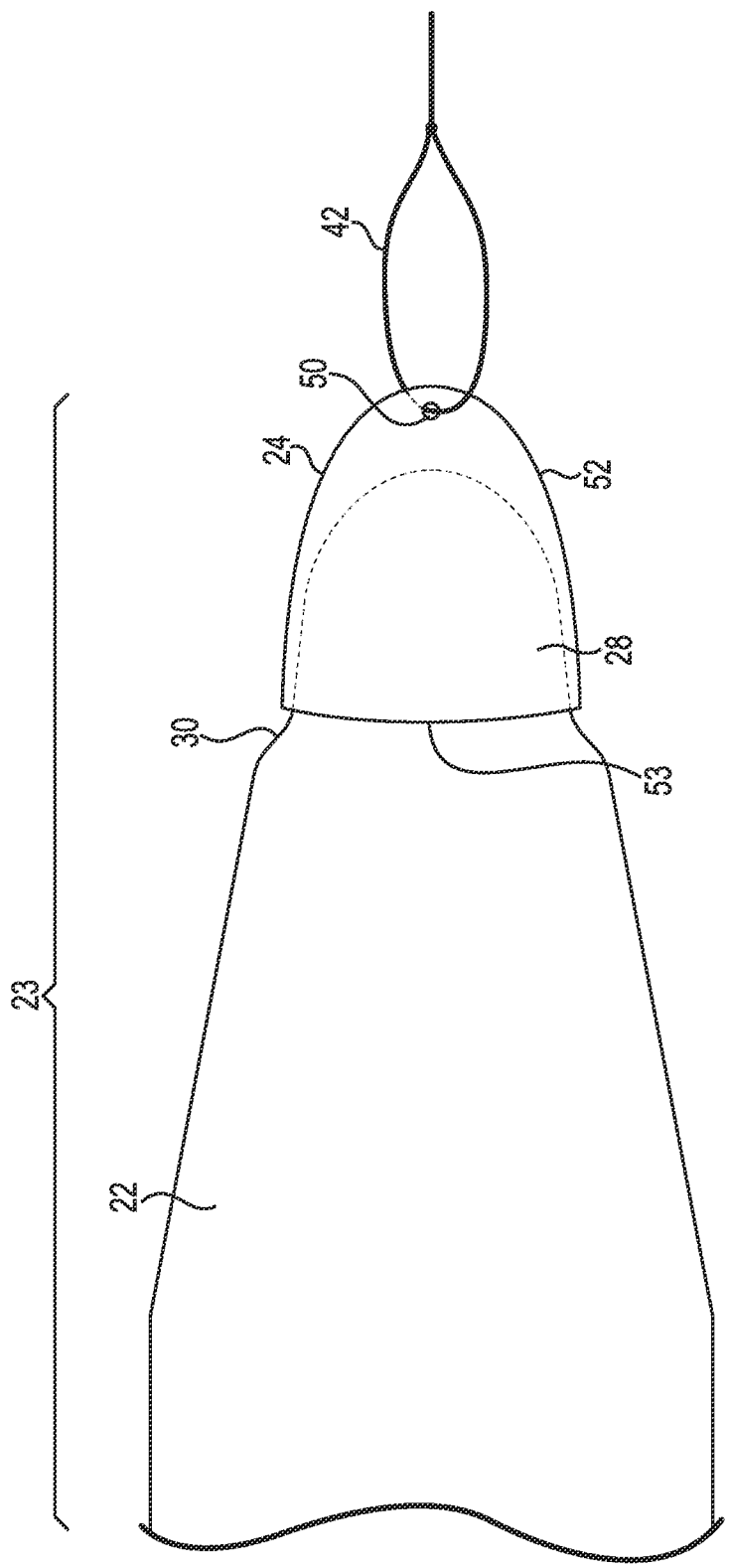

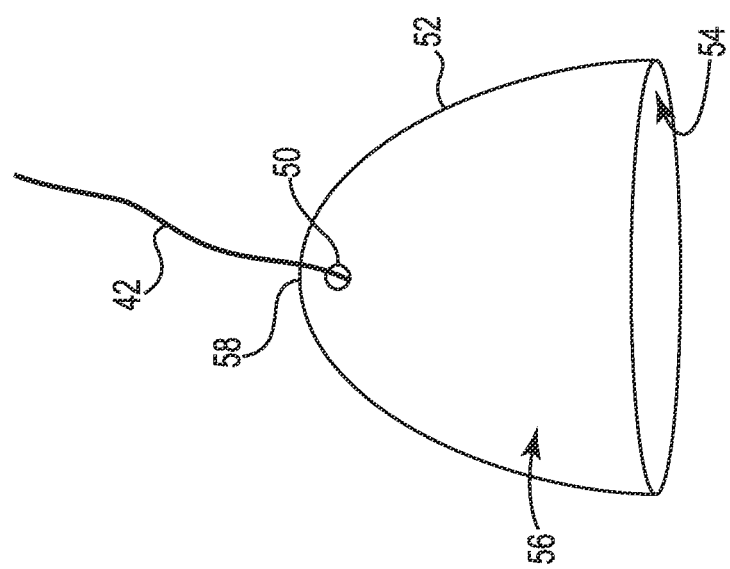

RESORBABLE SUTURE-ENGAGEMENT COMPONENT FOR A PENILE PROSTHETIC

BACKGROUND

An implanted penile prosthetic is effective in relieving erectile dysfunction in men.

An inflatable penile prosthetic typically includes a cylinder that is implanted in each corpora cavernosum of the penis, a fluid reservoir, and a pump with valve mechanisms to move fluid from the reservoir to the cylinder to create an erection in the penis. Other penile prosthetics include a malleable cylinder without inflation fluid.

Placement of a cylinder in the corpora cavernosum in a typical surgical procedure includes dilating the corpora cavernosum with a dilation tool to form an implant space sized to receive the cylinder. The cylinder is introduced into the implant space with a needle and a suture. One end of the suture is attached to the leading end of the cylinder and an opposite end of the suture is attached to a Keith needle. The Keith needle is directed through the glans penis and the cylinder is pulled distally towards the glans penis inside the corpora cavernosum.

The above-described penile prosthetics have proven effective in relieving erectile dysfunction in men. However, improvements to penile prostheses would be welcomed by surgeons and patients alike.

SUMMARY

One aspect provides a penile prosthetic including a cylinder that is implantable into a corpora cavernosum of a penis. A resorbable suture-engagement component is attached to an exterior surface of the cylinder.

One aspect provides an implantable penile prosthetic system including a pump attachable between a reservoir and an inflatable cylinder. The cylinder is configured to be placed in a corpora cavernosum of a penis. A resorbable suture-engagement component is attached to an exterior surface of the cylinder.

One aspect provides a penile prosthetic including a cylinder that is implantable into a corpora cavernosum of a penis, the cylinder having a wall that forms an exterior surface of the penile prosthetic. The wall extends from a proximal end portion to a distal end portion of the penile prosthetic. A suture-engaging component is attached to the exterior surface of the penile prosthetic. The suture-engaging component is resorbable into the tissue of the penis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2B is an enlarged end view of a distal end portion of the embodiment of FIG. 2A.

FIG. 3A is perspective view of a distal end portion of one embodiment of the suture-engaging component having a strand of tow suture attached to a ring.

FIG. 3C is perspective view of a distal end portion of one embodiment of the suture-engaging component in the form of a ring with two individual strands of tow suture attached to it.

FIG. 4A is an enlarged part cross-sectional view of a distal end portion of one embodiment of a penile prosthetic engaged by a suture.

FIG. 4B is an enlarged perspective view of one embodiment of a suture-engaging component.

DETAILED DESCRIPTION

Figure 1A:
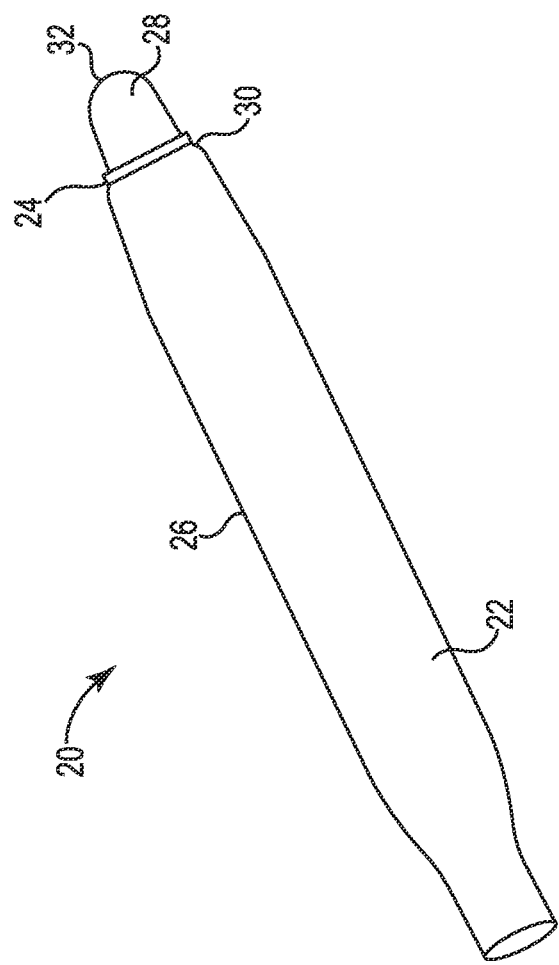
FIG. 1A is a perspective view of one embodiment of a distal portion of a penile prosthetic including a resorbable suture-engaging component.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

In this specification, "end" means endmost and "end portion" means that segment of a thing that is adjacent to and extends from the end.

In this specification, "substantially constant" in relation to a wall thickness means that the wall is configured to have equal thickness over a given area or portion except for production tolerances or acceptable variations in dimensions.

In this specification, "resorbable" characterizes a component or material that dissolves in body tissue of a patient over time. By "dissolves" is to be understood that the component or material is configured to lose its initial structural integrity and ceases to have significant coherence. In other words, once dissolved the component or material no longer provides a structural contribution to the penile prosthetic. The amount of time it takes for the component or material to dissolve is in dependency of the type of component or material and the dimensions thereof. It is useful if the component or material is dissolved at the end of a healing period after the implantation of the penile prosthetic. This will vary from patient to patient with different anatomies, but typically within 4-8 weeks post-surgery.

Experience has shown that higher satisfaction with penile prosthetics including one or two cylinders is obtained if the characteristics of the cylinder do not alter noticeably over the extent of the cylinder. This is likely because any alteration in such characteristics changes the "feel" of the erection that may be sensed by the patient or his partner during sexual activity. Improvements to penile prosthetic cylinders are possible if an end portion of the cylinder located in the distal-most part of the corpora cavernosum, adjacent the glans penis, is "filled" as much as possible to optimally expand that part of the corpora cavernosum (the front of the penis is expanded to the widest girth possible). Patient feedback indicates that optimized filling of the distal part of the corpora cavernosum provides a more natural feel of the erection. Sometimes a tip-piece or similar is utilized to optimize filling of the distal-most part of the corpora cavernosum.

Embodiments provide a penile prosthetic that is implantable into the corpora cavernosum of a penis. The penile prosthetic includes a cylinder and a resorbable suture-engaging component (RSEC). The RSEC attaches to an exterior surface of the cylinder. The RSEC is attachable to suture or a like material to assist the surgeon in implanting and adjusting the position of the cylinder in the corpora cavernosum. The RSEC is capable of subsequent biodegradation and absorption into the body of the patient, leaving the distal end portion of the cylinder unconstrained or unfettered by any form of a tip-piece. In embodiments wherein the cylinder in inflatable the unconstrained tip-piece of the cylinder expands as fully and naturally as the other portions of the cylinder to provide the user with a full and maximally expanded cylinder tip for improved girth and fullness in the area of the glans penis.

The RSEC allows the surgeon to place the cylinder in the penis with a familiar surgical approach. For example, the surgeon checks that one end of a suture (a tow suture) is engaged with the RSEC. The tow suture is led in the distal direction through the penis glans so that it is possible for the surgeon to pull the tow suture externally of the penis and move the cylinder in the distal direction, i.e. towards the distal-most part of the corpora cavernosum. The tow suture is pullable to move the cylinder in the distal direction and adjust it to optimally locate in, and fill, the distal-most part of the corpora cavernosum. The RSEC ensures that it is possible to engage the tow suture with the cylinder without providing a permanent attachment feature that undesirably changes the characteristics of the prosthetic.

Embodiments provide a penile prosthetic including a cylinder having a wall that forms an exterior surface of the penile prosthetic and extends from a proximal to a distal end of the penile prosthetic with an RSEC attached to the exterior surface.

Embodiments provide a penile prosthetic including an RSEC, which will dissolve inside the corpora cavernosum during the post-surgery healing time.

Embodiments provide a penile prosthetic that is easy to implant and adjust to optimally locate in and fill a distal-most part of the corpora cavernosum which provides an improved "feel" of the erection.

Embodiments provide an implantable penile prosthetic system including a pump attachable between a reservoir and an inflatable cylinder configured to be placed in a corpora cavernosum of a penis. An RSEC is attached to an exterior surface of the cylinder. The inflatable cylinder of the system is configured to be easily located in and fill a distal-most part of the corpora cavernosum to provide an improved "feel" of the erection.

Figure 1B:
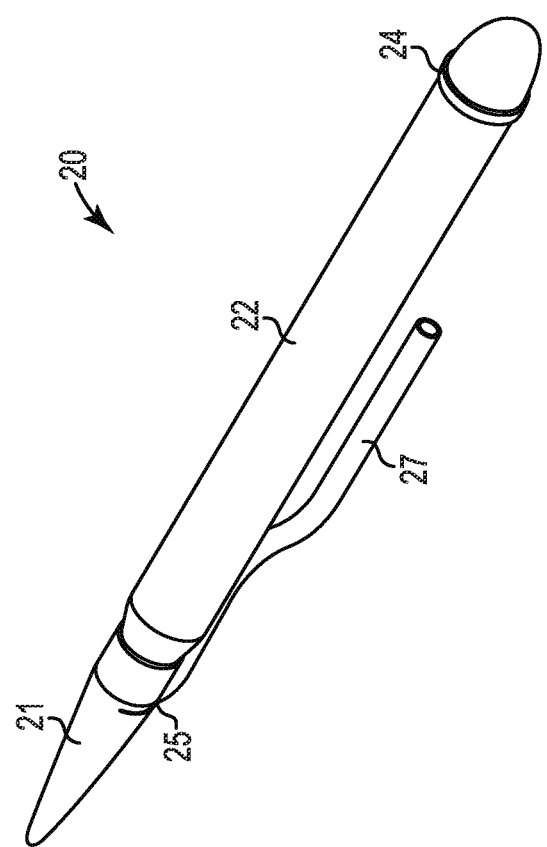
FIG. 1B is a perspective view of one embodiment of a penile prosthetic cylinder including a resorbable suture-engaging component.
Figure 1C:
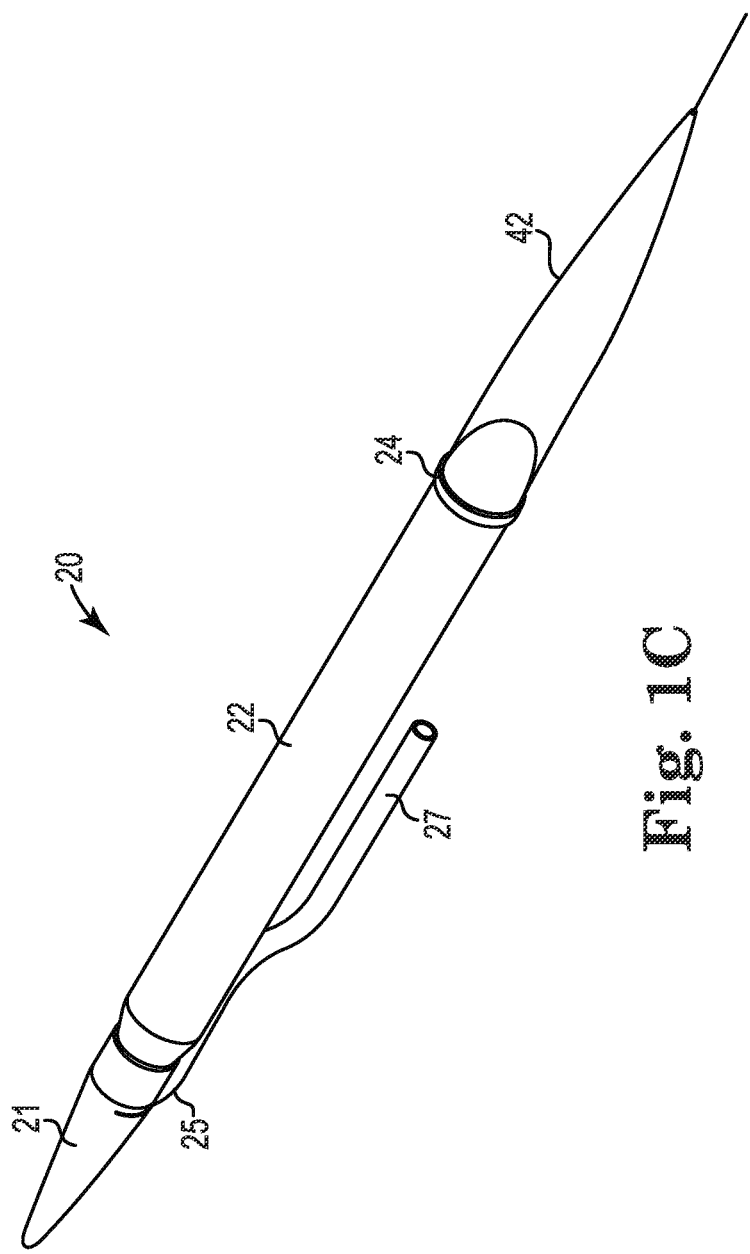
FIG. 1C is another perspective view of the embodiment of FIG. 1B in which the resorbable suture-engaging component is engaged by a suture.

FIG. 1A is a perspective view of one embodiment of a penile prosthetic 20. The penile prosthetic 20 includes a cylinder 22 and a resorbable suture-engaging component (RSEC) 24 is attached to an exterior surface 26 of the cylinder 22. In one embodiment, the RSEC 24 attaches to a distal end portion 28 of the cylinder 22. In one embodiment, the distal end portion 28 is located between an annular shoulder 30 and a distal end 32 of the cylinder 22. In one embodiment, the penile prosthetic 20 includes a rear tip 21 attached to the cylinder 22 and tubing 27 extending from a tubing junction 25 in the rear tip 21, as illustrated in FIG. 1B. FIG. 1C shows another perspective view of a cylinder as in FIG. 1B in which a suture 42 is engaged with the RSEC 24.

Figure 2A:
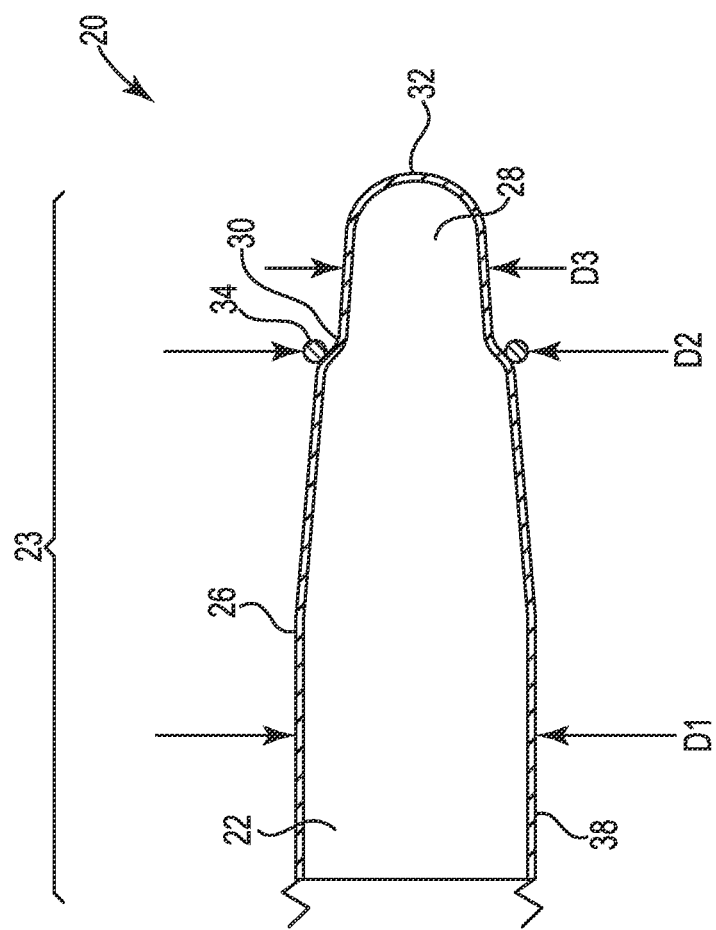
FIG. 2A is an enlarged part cross-sectional view of a distal end portion of the penile prosthetic illustrated in FIG. 1A.

FIG. 2A is an enlarged partial cross-sectional view of a distal portion 23 of one embodiment of the penile prosthetic 20 having a maximum diameter D1 of a main body portion 38 of the cylinder. In one embodiment, the RSEC includes a ring 34 attached annularly around the exterior surface 26 of the cylinder 22 and having a maximum outer diameter D2. In one embodiment, the ring 34 is offset a distance away from the distal end 32 of the cylinder 22. The distance is at most three times the measurement of a maximum outer diameter D3 of the distal end portion 28 of the cylinder 22. In one embodiment, the distal end portion 28 tapers distally from the annular shoulder 30 in a direction towards distal end 32, in which embodiment maximum diameter D3 is measured where the distal end portion 28 meets annular shoulder 30. In one embodiment, distal end portion 28 does not taper. In one embodiment, the ring 34 is attached to the exterior surface 26 at, or adjacent to, the annular shoulder 30. In one embodiment, the ring 34 is attached to the exterior surface 26 in a location proximal to the annular shoulder 30. In one embodiment, the ring 34 is attached to the exterior surface 26 distal to the annular shoulder 30, i.e. on the distal end portion 28 of the cylinder 22.

FIG. 2B is an enlarged end view of one embodiment of the distal portion 23 of the cylinder 22 as illustrated in FIG. 2A. The RSEC includes a ring 34 attached annularly around the distal end portion 28 of the cylinder 22 adjacent annular shoulder 30. For illustration purposes, in FIG. 2B a distance or space is visible between the ring 34 and the annular shoulder 30 indicating the ring 34 being in a location proximal to the annular shoulder 30. However, as presented above the ring 34 may also be located distal to the annular shoulder 30 in which case no distance/space would be visible between the ring 34 and the annular shoulder 30. In one embodiment, the distal end portion 28 of the cylinder 22 has a substantially constant thickness t.

FIG. 3A is a perspective view of a distal portion 23 of one embodiment of the penile prosthetic including a ring 34 attached to the cylinder 22 proximal to a distal end portion 28 of the cylinder. In one embodiment the ring 34 is engaged with a suture strand 42 extending through a pair of slots 50 provided in the ring with approximately 180 degrees of the ring between them. In one embodiment the ring 34 has a width and a thickness and defines and inner and an outer annular surface, the inner surface engaging with the cylinder 22.

Figure 3B:
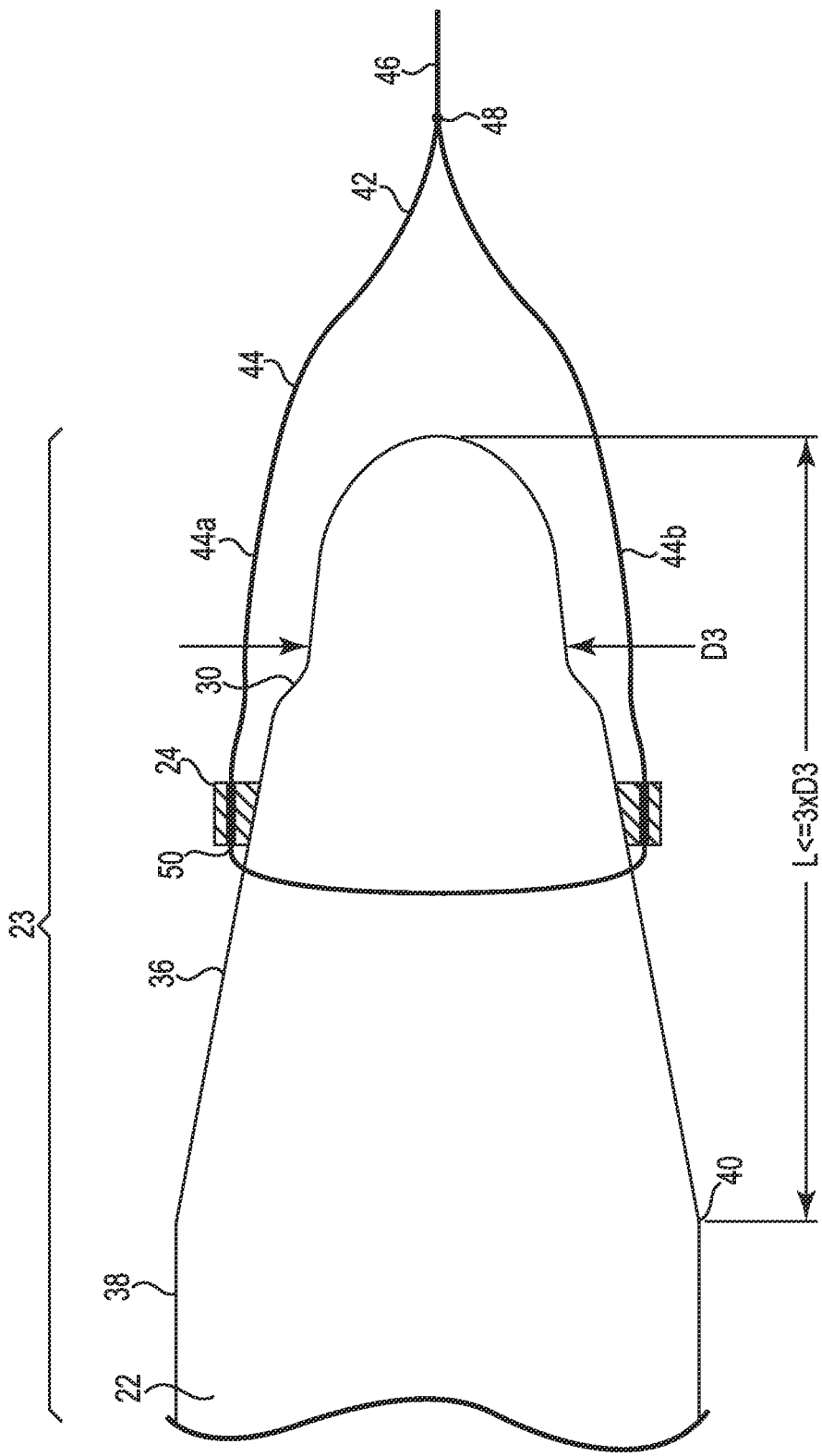
FIG. 3B is an enlarged part cross-sectional view of a ring attached to a distal end portion of one embodiment of a penile prosthetic.

FIG. 3B is an enlarged part cross-sectional view of a distal portion of one embodiment of the penile prosthetic 20. In one embodiment, distal portion 23 of the cylinder 22 includes a tapering segment 36 between an annular shoulder 30 and a main body portion 38 of the cylinder 22. In one embodiment, a proximal-most end 40 of the tapering segment 36 is located at a distance L of no more than three times the measurement of a maximum outer diameter D3 of the distal end portion 28 of the cylinder 22 (L≤3*D3). In the embodiment of FIG. 3B, the ring 34 is attached to the exterior surface 26 on tapering segment 36 within the distance L. Also shown is a suture 42 engaged with the RSEC 24. In one embodiment, the suture 42 includes a bifurcated portion 44 and a line portion 46 that may be connected in a knot 48. The bifurcated portion 44 includes arms 44a,44b that each engage with the RSEC 24. In one embodiment, the RSEC 24 is configured for bonding with one end of the length of suture 42. In one embodiment, the bond may be releasable. In one embodiment, the bond may be removable. In one embodiment, one end of the length of suture 42 is molded into engagement with the RSEC 24. In one embodiment, the RSEC 24 includes a slot 50 that receives and engages with a suture 42. In one embodiment, the slot 50 extends through the RSEC 24. In the embodiment shown, the suture 42 extends through one slot 50 and through another slot 50. One advantage is that this allows for use of a single strand of tow suture.

In one embodiment, shown in the perspective view of the distal portion 23 in FIG. 3C, one end of the length of suture 42 goes through the slot 50 and is tied on one side of the slot in a knot or ball 51 that is large enough not to slip through the slot 50. In one embodiment, the slot 50 in the resorbable material is configured to resorb quickly enough to allow for the knot or ball 51 to be pulled through the slot 50 for removal during the surgical procedure. In one embodiment, the length of suture 42 is engaged with the RSEC 24 during manufacture of the prosthetic. In one embodiment, the RSEC 24 is configured to be engaged with a suture by the surgeon or an assistant.

Figure 3D:
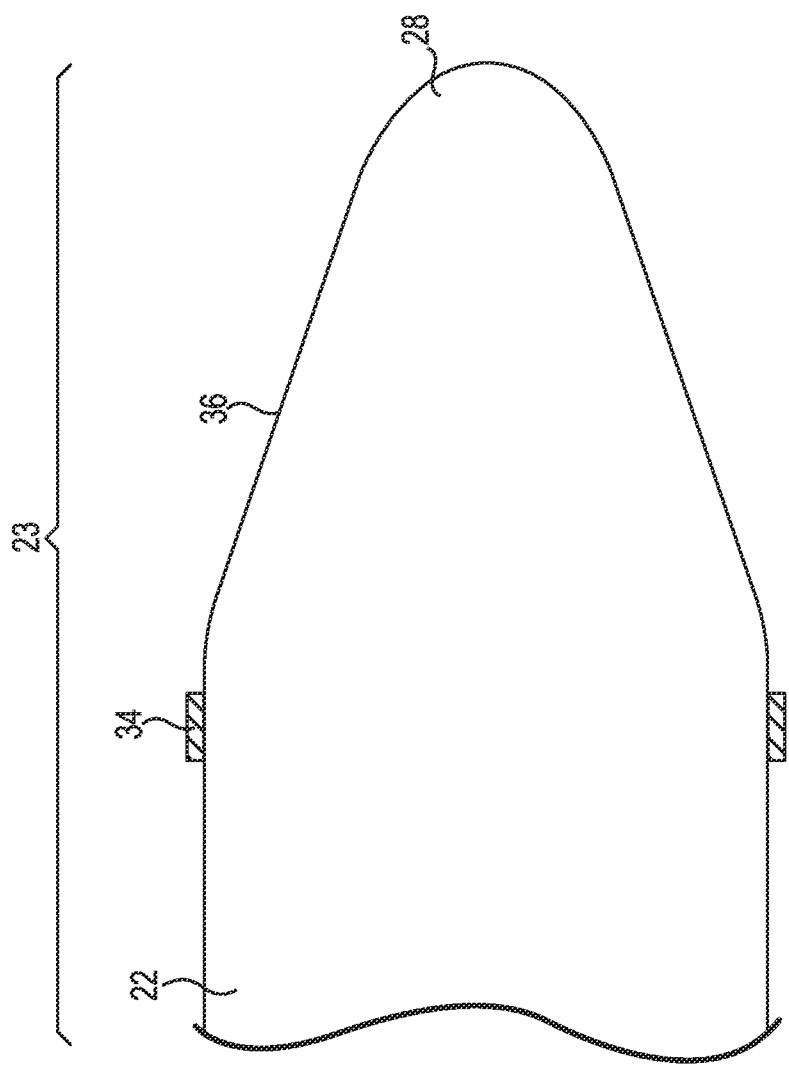
FIG. 3D is an enlarged part cross-sectional view of a ring attached to a distal end portion of one embodiment of a penile prosthetic.

FIG. 3D is an enlarged partial cross-sectional view of a distal portion of one embodiment of the penile prosthetic 20, in which the cylinder 22 does not include an annular shoulder such that tapering segment 36 transitions smoothly into distal end portion 28.

Figure 3E:
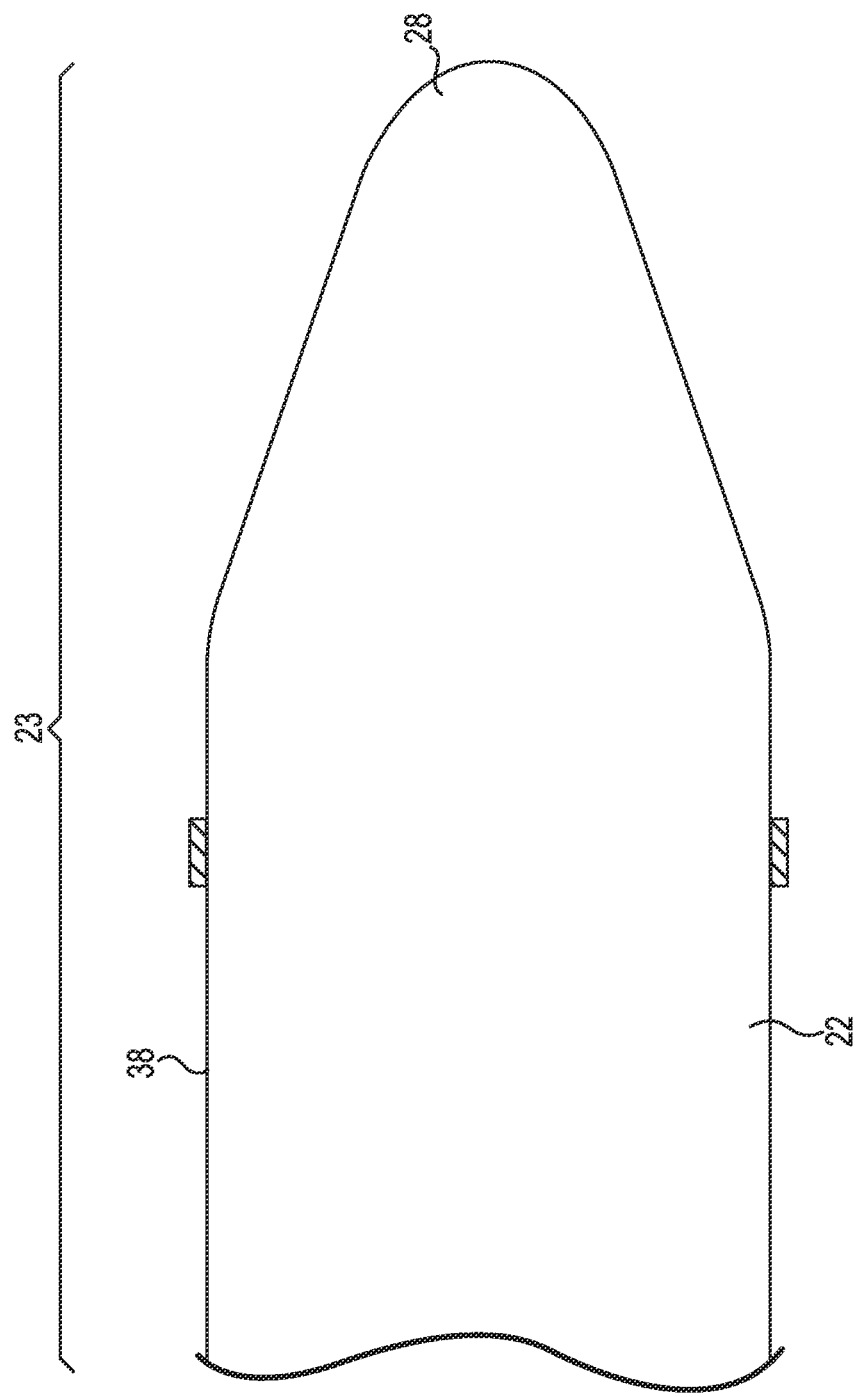
FIG. 3E is an enlarged part cross-sectional view of a distal end portion of one embodiment of a penile prosthetic.

FIG. 3E is an enlarged part cross-sectional view of a distal portion of one embodiment of the penile prosthetic 20. The distal end portion 28 is attached directly to the main body portion 38 and has the same diameter as the main body portion 38 at the location of attachment.

FIG. 4A is an enlarged part cross-sectional view of a distal portion 23 of one embodiment of the penile prosthetic 20. In one embodiment, the RSEC 24 includes a tip member 52 attached to the distal end portion 28 of the cylinder 22 (indicated in phantom line). The tip member 52 is resorbable. In one embodiment, the tip member 52 is attached to the distal end portion 28 by an adhesive. In one embodiment, the exterior surface 26 of the cylinder 22 is primed with a primer coating for adhesive attachment of the RSEC 24 to the cylinder 22. In one embodiment, a proximal end 53 of the tip member 52 abuts the annular shoulder 30. A suture 42 is shown engaging with the tip member 52 through a slot 50.

FIG. 4B is an enlarged perspective view of one embodiment of RSEC wherein the tip member 52 is configured as a thimble-like structure having an interior surface 54 configured to attach annularly around the distal end portion 28 of the cylinder 22. In one embodiment, the tip member 52 attaches to the cylinder 22 around less than an entirety of an exterior surface of the distal end portion 28. In one embodiment, the tip member 52 includes a slot 50 to receive suture 42. Other structures for receiving the suture and attaching it to the tip member 52 are acceptable including, but not limited to, an eye or a loop protruding from an exterior surface 56 of the tip member 52. A wall thickness of the resorbable material of the tip member 52 is one parameter for determining the time it takes before the resorbable tip member 52 loses structural integrity and eventually dissolves in the patient's body. A thicker wall will take longer time to dissolve than a thinner wall. In one embodiment, a portion of the wall of the tip member 52 adjacent to an apex 58 of the tip member has an increased material thickness to accommodate the slot 50.

In one embodiment, the RSEC 24 is bonded to the exterior surface 26 of the cylinder 22. In one embodiment, the RSEC is releasably bonded to the exterior surface 26 of the cylinder 22. In one embodiment, the RSEC is removably bonded to the exterior surface 26 of the cylinder 22.

Figure 5:
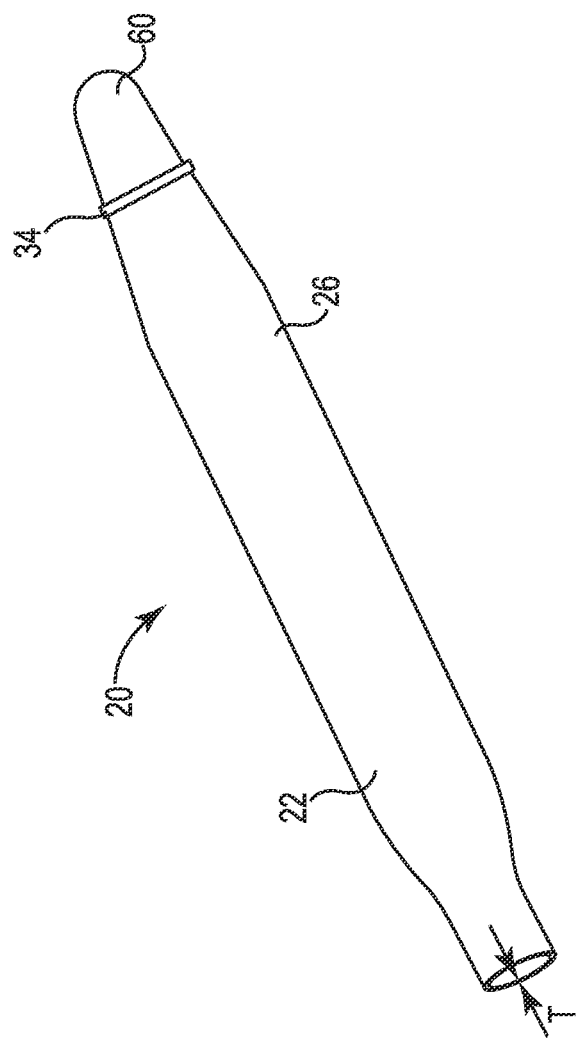
FIG. 5 is a perspective view of one embodiment of a penile prosthetic including a resorbable suture-engaging component and a tip component.

FIG. 5 is a perspective view of one embodiment of a penile prosthetic 20 including a cylinder 22 suitable for implantation into a corpora cavernosum of a penis. An RSEC 24 configured as a ring 34 is attached to an exterior surface 26 of the cylinder 22. In one embodiment, the penile prosthetic 20 includes a tip component 60. In one embodiment, the tip component 60 is manufactured from a silicone material. In one embodiment, the ring 34 is attached to the cylinder 22 proximal to the tip component 60. The tip component 60 is useful for providing additional filling of the distal-most part of the corpora cavernosum. By using a silicone material for the tip component 60, the gain in erection "feel" due to the additional filling is achieved with a soft material. This provides a penile prosthetic with no sudden change in characteristics and with a desirable softness of the penile prosthetic in the distal part of the corpora cavernosum adjacent or contacting the glans penis to the benefit of the erection feel for both the patient and his sexual partner. In one embodiment, the cylinder 22 has a uniform wall thickness T, i.e. the cylinder wall has the same thickness over its entirety.

Figure 6:
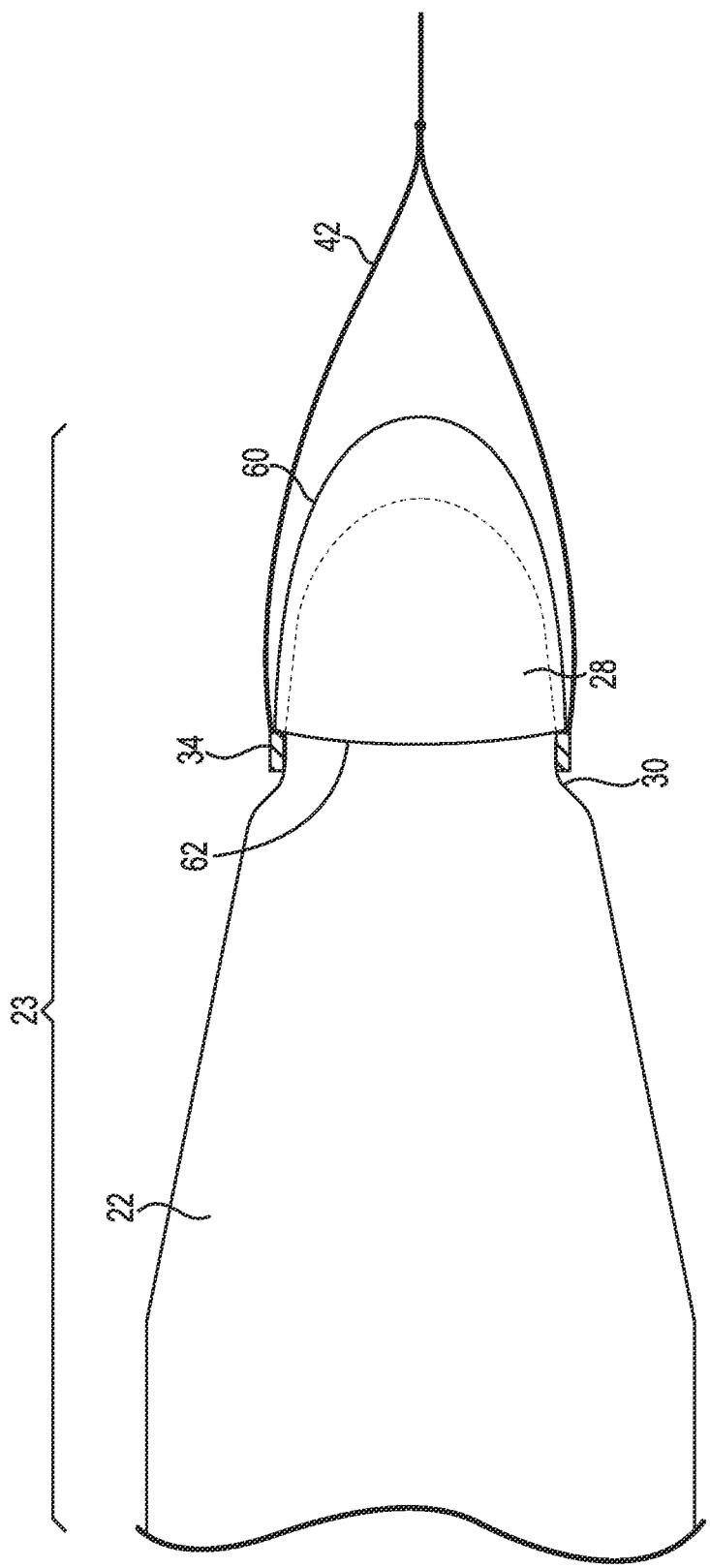
FIG. 6 is an enlarged part cross-sectional view of a distal end portion of one embodiment of a penile prosthetic also showing a tip component and a suture.

FIG. 6 is an enlarged part cross-sectional view of a distal portion 23 of one embodiment of a penile prosthesis 20. In one embodiment, an RSEC including a ring 34 is attached to the cylinder 22 at the annular shoulder 30. In one embodiment, a tip component 60 is attached to a distal end portion 28 of the cylinder 22 distal to the ring 34. In one embodiment, a proximal end 62 of the tip component abuts the ring 34. A suture 42 engaged with the ring 34 is shown extending in a distal direction from the ring 34.

Figure 7:
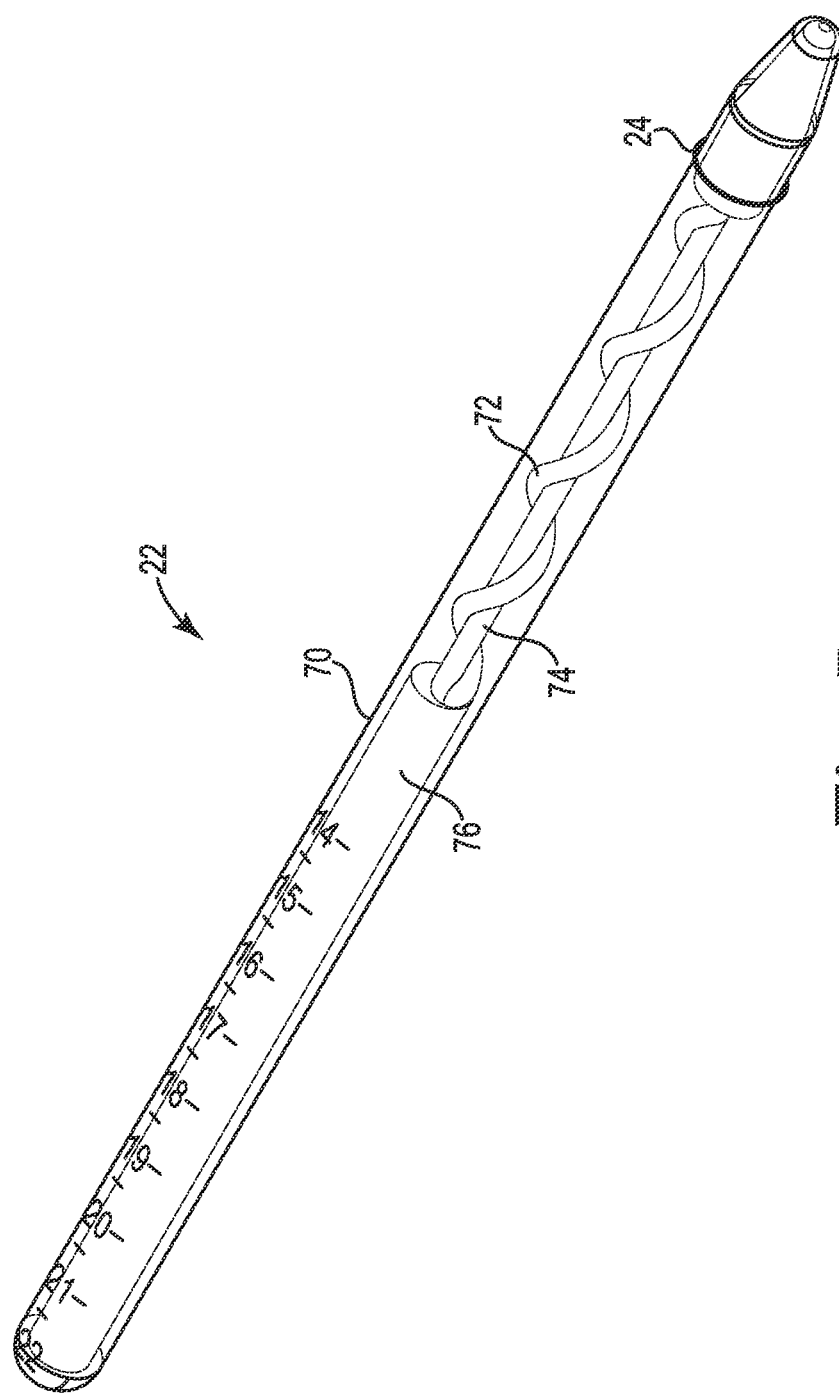
FIG. 7 is a perspective view of one embodiment of a penile prosthetic wherein the cylinder is malleable.

FIG. 7 is a perspective view of one embodiment wherein the cylinder 22 is a malleable cylinder including a silicone elastomer shaft 70 and a silver wire coil 72 configured to be placed around a silver wire core 74 with a portion of the core and coil wrapped in a polymer 76 such as urethane and at least one other portion wrapped in a polymer such as a polyester or a polyethylene terephthalate. Both segments are over-molded with a silicone rubber. It is useful to apply a hydrophilic coating to the exterior surface of the silicone rubber. Suitable malleable cylinders are available from Coloplast Corp., Minneapolis, Minn.

Figure 8:
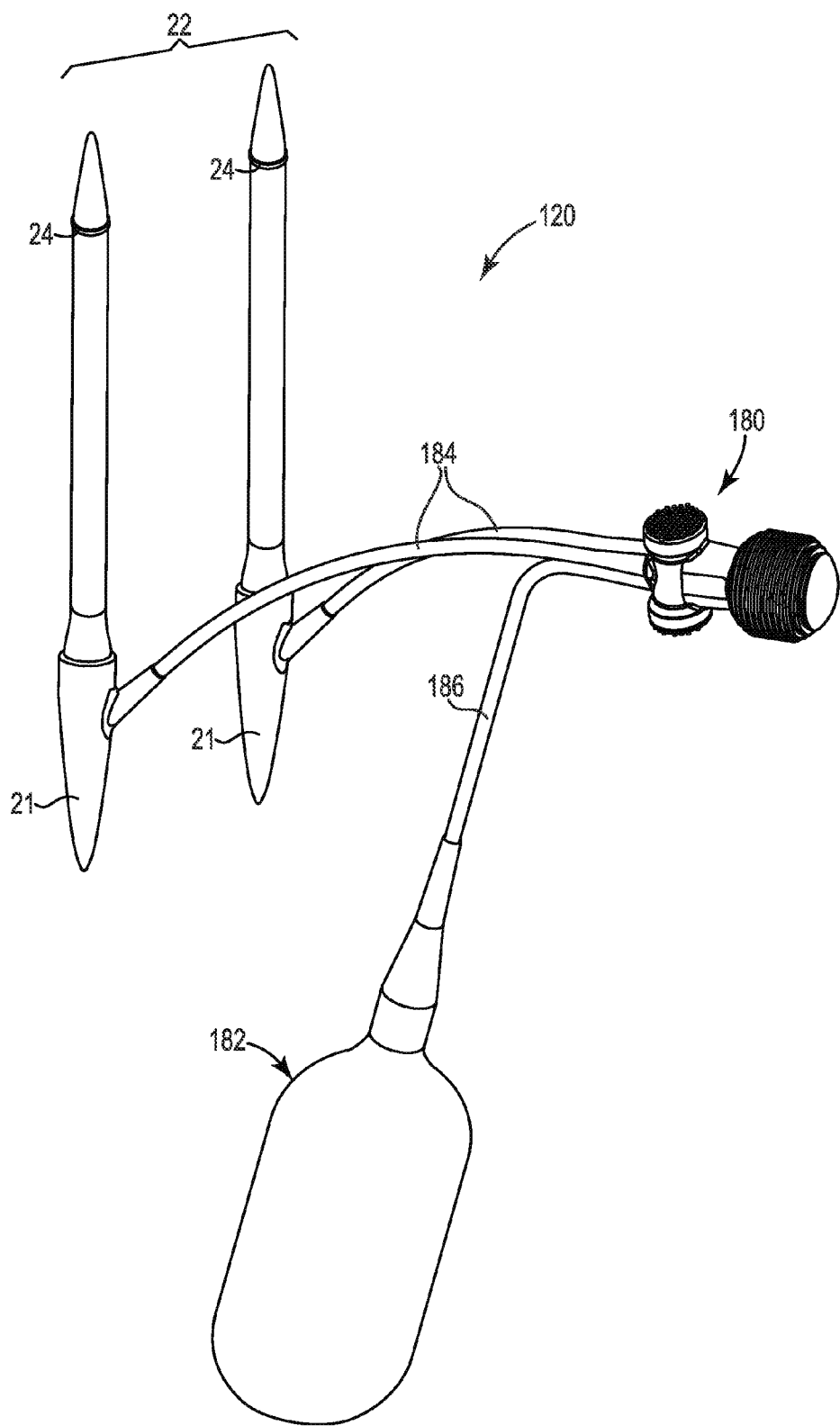
FIG. 8 is a perspective view of one embodiment of a penile prosthetic system including a pump connected between a reservoir and a cylinder, the cylinder including a resorbable suture-engaging component.

FIG. 8 is a perspective view of one embodiment of a penile prosthetic system 120 including a pump 180 connected between a liquid reservoir 182 and an inflatable cylinder 22, the cylinder 22 including a resorbable suture-engaging component (RSEC) 24. Tubing 184,186 connects the pump and the cylinders, and the pump and the reservoir, respectively. In one embodiment, the tubing 184 communicates with the inflatable cylinder 22 through a rear tip 21. In one embodiment, the system 120 includes two individual inflatable cylinders 22. Pressure on the pump 180 causes flow of liquid from the reservoir 182 to the cylinders 22 to create an erection in the penis. The pump 180 can include a valve activatable to release the liquid from the cylinders 22 to flow back to the reservoir 182.

In one embodiment, the cylinder of the penile prosthetic is inflatable. Suitable materials for fabricating the inflatable cylinder include silicone, polymers such as urethanes, blends of polymers with urethane, copolymers of urethane, or the like. Suitable inflatable cylinders are available from Coloplast Corp., Minneapolis, Minn. In one embodiment, the pump and the reservoir are fabricated from material suitable for body implantation, such as silicone or the urethane-based materials described above for the cylinder.

In embodiments wherein the cylinder 22 is inflatable, using the RSEC 24 for the implantation procedure provides an additional advantage in the subsequent post healing time use of the prosthetic. The advantage includes that the distal end portion 28 is capable of the same level of expansion as the remaining part of the cylinder 22 because no permanent suture attachment feature is necessary near or at the distal end portion 28. As the inflatable cylinder 22 is capable of expanding equally throughout its extent, the "feel" of the erection is more natural. Also, the part of the prosthetic located in the distal most part of the corpora cavernosum has the same characteristics as the rest of the prosthetic while better filling the space of the corpora cavernosum at, or adjacent to, the glans penis.

Suitable materials for the resorbable suture-engaging component include polyester urethane (PEU), polycaprolactone (PCL), polyglycolic acid (PGA), polylactic acid (PLLA), polydioxanone (PDO) and various copolymers of these.

Attachment of the RSEC 24 to the cylinder 22 may be achieved in different ways, including adhesively bond the RSEC 24 onto the cylinder by a solvent bond or using a PU adhesive in embodiments wherein the cylinder too is manufactured from a PU. In one embodiment, the RSEC 24 is directly built up from resorbable PEU liquid precursors on the PU surface of the cylinder instead of the RSEC 24 being separately provided and attached. In one embodiment, the RSEC 24 is provided as a ring 34 that is mechanically adhered by making an inner diameter of the ring 34 slightly smaller than an outer diameter of the cylinder 22 (at the desired location of attachment). By application of a solvent to the ring, the ring swells which allows it to be placed around the cylinder surface. When the solvent vaporizes the ring shrinks back down and adheres through mechanical and Van der Waals forces.

Embodiments have been described in which a penile prosthetic includes a resorbable component for engagement with a suture used to tow the penile prosthetic distally into the corpora cavernosum of a penis. The resorbable component dissolves over the post-surgery heal time and provides for the penile prosthetic to be easily locatable and adjustable without necessitating permanent suture attachment features on the prosthetic to enable the surgeon to pull the prosthetic distally. This in turn ensures a penile prosthetic with little or no influence on the characteristics over the longitudinal extent of the surface of the penile prosthetic.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A penile prosthetic comprising:
a cylinder that is implantable into a corpora cavernosum of a penis and a resorbable suture-engagement component attached to an exterior surface of the cylinder.

2. The penile prosthetic of claim 1, wherein the suture-engagement component is attached to a distal end portion of the cylinder.

3. The penile prosthetic of claim 1, wherein the suture-engagement component comprises a ring attached annularly around the exterior surface of the cylinder.

4. The penile prosthetic of claim 3, wherein the ring is offset a distance away from a distal end of the cylinder, the distance being no more than three times the measurement of a maximum outer diameter of a distal end portion of the cylinder.

5. The penile prosthetic of claim 1, wherein the suture-engagement component comprises a tip member attached to a distal end of the cylinder.

6. The penile prosthetic of claim 1, wherein the suture-engagement component is sized to have a second outer diameter that does not exceed a first outer diameter of the cylinder.

7. The penile prosthetic of claim 1, wherein the suture-engagement component is configured for bonding with a suture.

8. The penile prosthetic of claim 1, wherein the suture-engagement component comprises one or more slots configured to receive a suture.

9. The penile prosthetic of claim 8, comprising at least two sutures, each of the sutures received in an individual one of the slots.

10. The penile prosthetic of any one of claims 7-9, wherein one end of the suture is engaged with the suture-engagement component.

11. The penile prosthetic of claim 1, wherein a wall thickness of a distal end portion of the cylinder is substantially constant.

12. The penile prosthetic of claim 1, wherein the cylinder has a uniform wall thickness.

13. The penile prosthetic of claim 1, further comprising a tip component attached to a distal end portion of the cylinder.

14. The penile prosthetic of claim 13, wherein the tip component is manufactured from a silicone material.

15. The penile prosthetic of claim 1, wherein the cylinder is inflatable.

16. The penile prosthetic of claim 1, wherein the cylinder is malleable.

17. An implantable penile prosthetic system comprising:
a pump attachable between a reservoir and an inflatable cylinder that is configured to be placed in a corpora cavernosum of a penis,
wherein a resorbable suture-engagement component is attached to an exterior surface of the cylinder.

18. The penile prosthetic system of claim 17, wherein a wall thickness of a distal end portion of the cylinder is substantially constant.

19. The penile prosthetic system of claim 17, wherein the suture-engagement component comprises a ring attached annularly around the exterior surface of the cylinder.

20. The penile prosthetic system of claim 17, wherein the suture-engagement component comprises a tip member attached to a distal end of the cylinder.

21. A penile prosthetic comprising:
a cylinder that is implantable into a corpora cavernosum of a penis, the cylinder having a wall that forms an exterior surface of the penile prosthetic, the wall extending from a proximal end portion of the penile prosthetic to a distal end of the penile prosthetic; and
a suture-engaging component attached to the exterior surface of the penile prosthetic;
wherein the suture-engaging component is resorbable into tissue of the penis.

22. The penile prosthetic of claim 21, wherein the suture-engaging component is bonded to the exterior surface of the penile prosthetic.

23. The penile prosthetic of claim 22, wherein the suture-engaging component is releasably bonded to the exterior surface of the penile prosthetic.

24. The penile prosthetic of claim 22, wherein the suture-engaging component is removably bonded to the exterior surface of the penile prosthetic.

25. The penile prosthetic of claim 21, wherein the suture-engaging component is attached to a distal end portion of the cylinder.

* * * * *